US008906653B2

(12) United States Patent
Völkert et al.

(10) Patent No.: US 8,906,653 B2
(45) Date of Patent: Dec. 9, 2014

(54) METHOD FOR FERMENTATIVELY PRODUCING 1,5-DIAMINOPENTANE

(75) Inventors: Martin Völkert, Ludwigshafen (DE); Oskar Zelder, Speyer (DE); Burkhard Ernst, Mannheim (DE); Weol Kyu Jeong, Gunsan (KR)

(73) Assignee: BASF SE, Ludwigshafen (DE)

( * ) Notice: Subject to any disclaimer, the term of this patent is extended or adjusted under 35 U.S.C. 154(b) by 389 days.

(21) Appl. No.: 12/864,176

(22) PCT Filed: Jan. 23, 2009

(86) PCT No.: PCT/EP2009/050778
§ 371 (c)(1),
(2), (4) Date: Jul. 22, 2010

(87) PCT Pub. No.: WO2009/092793
PCT Pub. Date: Jul. 30, 2009

(65) Prior Publication Data
US 2010/0292429 A1   Nov. 18, 2010

(30) Foreign Application Priority Data
Jan. 23, 2008   (EP) .................................... 08150575

(51) Int. Cl.
*C12P 13/00* (2006.01)
*C08G 73/00* (2006.01)
*C02F 3/00* (2006.01)
*C07C 209/84* (2006.01)

(52) U.S. Cl.
CPC ............. *C12P 13/001* (2013.01); *C07C 209/84* (2013.01)
USPC ............................ 435/128; 528/422; 210/601

(58) Field of Classification Search
None
See application file for complete search history.

(56) References Cited

U.S. PATENT DOCUMENTS

| 4,489,160 | A | 12/1984 | Katsumata et al. |
| 4,601,893 | A | 7/1986 | Cardinal |
| 5,158,891 | A | 10/1992 | Takeda et al. |
| 5,175,108 | A | 12/1992 | Bachmann et al. |
| 5,965,391 | A | 10/1999 | Reinscheid et al. |
| 6,238,896 | B1 | 5/2001 | Ozaki et al. |
| 2008/0268502 | A1 | 10/2008 | Haefner et al. |
| 2009/0246838 | A1 | 10/2009 | Zelder et al. |
| 2009/0292100 | A1 | 11/2009 | Fiene et al. |
| 2009/0325244 | A1 | 12/2009 | Herold et al. |
| 2010/0041107 | A1 | 2/2010 | Herold et al. |
| 2010/0331461 | A1 | 12/2010 | Yamamoto et al. |

FOREIGN PATENT DOCUMENTS

| EP | 325030 A2 * | 7/1989 |
| EP | 0472869 A2 | 3/1992 |
| EP | 1482055 A1 | 12/2004 |
| JP | 10229891 A | 9/1998 |
| JP | 2002-223771 A | 8/2002 |
| JP | 2004-000114 A | 1/2004 |
| JP | 2004-208646 A | 7/2004 |
| JP | 2004-222569 A | 8/2004 |
| WO | WO-96/15246 A1 | 5/1996 |
| WO | WO-2006/069711 A1 | 7/2006 |
| WO | WO-2006/123778 A1 | 11/2006 |
| WO | WO 2006123778 A1 * | 11/2006 |
| WO | WO-2007/113127 A1 | 10/2007 |
| WO | WO-2007/135188 A2 | 11/2007 |
| WO | WO-2008/080900 A2 | 7/2008 |
| WO | WO-2008/101850 A1 | 8/2008 |
| WO | WO-2008/101857 A2 | 8/2008 |
| WO | WO-2008/152016 A1 | 12/2008 |
| WO | WO-2009/095440 A1 | 8/2009 |
| WO | WO-2009/098046 A1 | 8/2009 |

OTHER PUBLICATIONS

Mandelstam, J. "Induced Biosynthesis of Lysine Decarboxylase in *Bacterium cadaveris*" (1954). J. Gen. Microbiol. 11, 426-437.*
USPTO provided english translation for JP 2004000114, by Takashi et al., performed Sep. 2011, 35 pages.*
English Translation for for WO 2006/123778, provided by the USPTO Aug. 2011, 42 pages.*
N. Ogata and Y. Hosoda "Synthesis of Hydrophilic Polyamide from L-Tartarate and Diamines by Active Polycondensation" Journal of Polymer Science Polymer Chemistry Edition vol. 13,1793-1801 (1975).*
Stephanie L. Kwolek and Paul W. Morgan "Preparation of Polyamides, Polyurethanes, Polysulfonamides, and Polyesters by Low Temperature Solution Polycondensation" Journal of Polymer Science: Part A vol. 2, pp. 2693-2703 (1964).*
Eikmanns, B.J., et al., "A Family of *Corynebacterium glutamicum/Escherichia coli* Shuttle Vectors for Cloning, Controlled Gene Expression, and Promoter Probing", Gene, 1991, vol. 102, pp. 93-98.
Guerrero, C., et al., "Directed Mutagenesis of Regulatory Palindromic Sequence Upstream from the *Brevibacterium lactofermentum* tryptophan Operon", Gene, 1994, vol. 138, pp. 35-41.
Jensen, P.R., et al., "Artificial Promoters for Metabolic Optimization", Biotech and Bioengineering, 1998, vol. 58, Nos. 2 and 3, pp. 191-195.
Labarre, J., et al., "Gene Replacement, Integration and Amplification at the *gdhA* Locus of *Corynebacterium glutamicum*", Journal of Bacteriology, 1993, vol. 175, No. 4, pp. 1001-1007.
Makrides, S.C., et al., "Strategies for Achieving High-Level Expression of Genes in *Escherichia coli*", Microbiological Reviews, 1996, vol. 60, No. 3, pp. 512-538.

(Continued)

*Primary Examiner* — Thane Underdahl
(74) *Attorney, Agent, or Firm* — Drinker Biddle & Reath LLP

(57) ABSTRACT

The invention relates to a method for isolating 1,5-diaminopentane (DAP) from DAP-containing fermentation broths, to a method for the fermentative production of DAP using said isolating method and to a method for producing DAP-comprising polymers by using the DAP isolated or fermatively produced DAPs according to said methods.

20 Claims, 2 Drawing Sheets

(56) References Cited

OTHER PUBLICATIONS

Malumbres, M., et al., "Codon Preference in Corynebacteria", Gene, 1993, vol. 134, pp. 15-24.

Menkel, E., et al., "Influence of Increased Aspartate Availability on Lysine Formation by a Recombinant Strain of *Corynebacterium glutamicum* and Utilization of Fumarate", Applied and Environmental Microbiology, 1989, vol. 55, No. 3, pp. 684-688.

Motoyama, H., et al., "Overproduction of L-Lysine from Methanol by *Methylobacillus glycogenes* Derivatives Carrying a Plasmid with a Mutated *dapA* Gene", Applied and Environmental Microbiology, 2001, vol. 67, No. 7, pp. 3064-3070.

Patek, M., et al., "Promoters from *Corynebacterium glutamicum*: Cloning, Molecular Analysis and Search for a Consensus Motif", Microbiology, 1996, vol. 142, pp. 1297-1309.

Reinscheid, D.J., et al., "Stable Expression of *hom-1-thrB* in *Corynebacterium glutamicum* and Its Effects on the Carbon Flux to Threonine and Related Amino Acids", Applied and Environmental Microbiology, 1994, vol. 60, No. 1, pp. 126-132.

Schaefer, A. et al., "Small Mobilizable Multi-Purpose Cloning Vectors Derived from the *Escherichia coli* Plasmids pK18 and pK19: selection of defined deletions in the Chromosome of *Corynebacterium glutamicum*", Gene, 1994, vol. 145, pp. 69-73.

Schrumpf, B., et al., "A Functionally Split Pathway for Lysine Synthesis in *Corynebacterium glutamicum*", Journal of Bacteriology, 1991, vol. 173, No. 14, pp. 4510-4516.

Serwold-Davis, T.M., et al., "Localization of an Origin of Replication in *Corynebacterium diphtheriae* Broad Host range Plasmid pNG2 that also Functions in *Escherichia coli*", FEMS Microbiology Letters, 1990, vol. 66, pp. 119-124.

Simon, R., et al., "A Broad Host Range Mobilization System for In Vivo Genetic Engineering: Transposon Mutagenesis in Gram Negative Bacteria", Bio/Technology, 1983, pp. 784-791.

Sonnen, H., et al., "Characterization of pGA1, a New Plasmid from *Corynebacterium glutamicum* LP-6", Gene, 1991, vol. 107, pp. 69-74.

Spratt, B.G., et al., "Kanamycin-resistant Vectors that are Analogues of Plasmids pUC8, pUC9, pEMBL8 and pEMBL9", Gene, 1986, vol. 41, pp. 337-342.

Tauch, A., et al., "*Corynebacterium glutamicum* DNA is subjected to methylation-restriction in *Escherichia coli*", FEMS Microbiology Letters, 1994, vol. 123, pp. 343-348.

Thierbach, G., et al,, "Transformation of Spheroplasts and Protoplasts of *Corynebacteriumum glutamicum*", Applied Microbiol Biotechnol, 1988, vol. 29, pp. 356-362.

Eikmanns, B.J., et al., "Molecular Aspects of lysine, threonine, and isoleucine biosynthesis in *Corynebacterium glutamicum*", Antonie van Leeuwenhock, 1993, vol. 64, pp. 145-163.

Dunican, L.K., et al., "High Frequency Transformation of Whole Cells of Amino Acid Producing Coryneform Bacteria Using High Voltage Electroporation", Bio/Technology, 1989, vol. 7, p. 1067-1070.

Bernard, P., et al., "The F Plasmid CcdB Protein Induces Efficient ATP-Dependent DNA Cleavage by Gyrase", J. Mol. Biol., 1993, vol. 234, pp. 534-541.

Martin, J.F., et al., "Cloning Systems in Amino Acid-Producing Corynebacteria", Bio/Technology, 1987, vol. 5, pp. 137-146.

Schwarzer, A., et al., "Manipulation of *Corynebacterium glutamicum* by Gene Disruption and Replacement", Bio/Technology, 1991, vol. 9, pp. 84-87.

Tsuchiya, M., et al., "Genetic Control Systems of *Escherichia coli* can Confer Inducible Expression of Cloned Genes in Coryneform Bacteria", Bio/Technology, 1988, vol. 6, pp. 428-430.

\* cited by examiner

METHOD FOR FERMENTATIVELY PRODUCING 1,5-DIAMINOPENTANE

RELATED APPLICATIONS

This application is a national stage application (under 35 U.S.C. §371) of PCT/EP2009/050778, filed Jan. 23, 2009, which claims benefit of European application 08150575.2, filed Jan. 23, 2008.

The present invention relates to a process for isolating 1,5-diaminopentane (DAP) from DAP-comprising fermentation broths, to a process for the fermentative production of DAP using said isolation method and to a process for preparing DAP-comprising polymers by employing the DAP isolated and fermentatively produced in this manner.

BACKGROUND OF THE INVENTION 1,5-Diaminopentane (frequently also referred to as pentamethylenediamine or cadaverine; referred to as DAP hereinbelow) is an important raw material in the chemical industry. DAP is used, for example, in the preparation of polyamides, polyureas or polyurethanes and of copolymers thereof.

Moreover, the fermentative or enzymatic production of DAP via lysine decarboxylation has been known for some time. Various processes for isolating the product of interest from the fermentation broth have been described in this context.

EP-A-1 482 055, for example, describes the enzymatic decarboxylation of lysine in the presence of a dicarboxylic acid for adjusting the pH during the reaction. The DAP dicarboxylate produced in the process is isolated by firstly decolorizing and concentrating the solution comprising the product of interest and then crystallizing DAP dicarboxylate in a cooling crystallization process.

WO-A-2006/123778 describes the preparation of DAP carbonate by enzymatic decarboxylation of lysine in the presence of carbon dioxide. DAP is formed by concentrating the reaction solution and eliminating carbon dioxide.

JP 2004-208 646 describes the preparation of DAP dicarboxylate by enzymatic decarboxylation of a solution comprising L-lysine dicarboxylate and precipitation of DAP dicarboxylate by adding an organic solvent selected from among alcohols, ketones and nitriles.

JP 2004-222 569 describes the preparation of DAP by employing a coryneform bacterium expressing L-lysine decarboxylase, adjusting the culture supernatant to pH 12 and extracting DAP with a polar organic solvent.

Finally, JP 2004-000 114 describes the preparation of DAP by converting highly concentrated L-lysine monohydrochloride using *E. coli* cells expressing L-lysine decarboxylase, adjusting the reaction solution to pH and extracting the reaction product with a polar organic solvent followed by distillation.

However, the prior art processes based on DAP extraction with the aid of an organic solvent are particularly disadvantageous in that the yield of product of interest is suboptimal and the extraction step in particular is too slow and the overall process is too time-consuming, this being greatly disadvantageous to applying said preparation on an industrial scale.

BRIEF DESCRIPTION OF THE INVENTION

The object of the present invention is therefore to further improve the isolation of DAP (cadaverine) from fermentation broths. More specifically, it is intended to further increase the yield of product of interest and improve on the time required for isolation, in particular solvent-based extraction.

Surprisingly, this object was achieved by providing a process wherein a) the fermentation broth is first adjusted to an alkaline pH, then thermally treated, and extracted thereafter with a suitable organic extractant. DAP-comprising byproducts of the fermentation, in particular acetyl-DAP, were surprisingly found here to be cleaved hydrolytically with liberation of the product of interest. Another surprise was the finding that the rate of phase separation in the extraction step can be increased substantially. This increased rate of phase separation is particularly evident with the work-up of fermentation broths from fermentation of microorganisms in the presence of complex nutrient media such as yeast extract, for example.

DETAILED DESCRIPTION OF THE INVENTION

1. Preferred Embodiments

Figure 1:
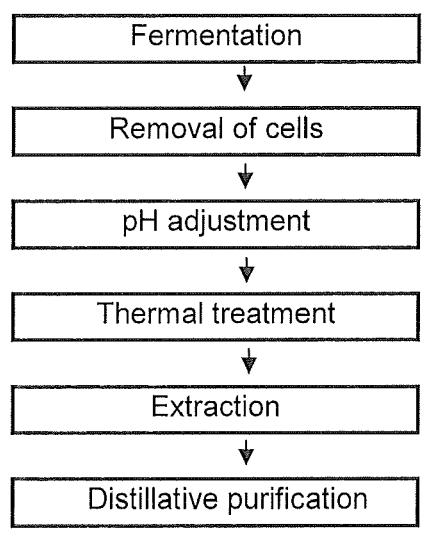
FIG. 1 depicts a flow diagram of a special embodiment of the invention of an overall process for isolating DAP from a fermentation broth.

The invention relates to a process for isolating 1,5-diaminopentane (DAP) from a DAP-comprising fermentation broth, wherein a) the fermentation broth is alkalized, b) the fermentation broth is thermally treated, c) DAP is extracted with an organic extractant, and d) DAP is isolated from the removed organic phase.

In a first special development of the process, the fermentation broth is adjusted to a pH of >11, such as in particular ≥11.5 or ≤12, such as in particular ≤12 to 14, or 12.5 to 13.8, or 13 to 13.8, or 13.5 to 13.7. For this purpose, the pH is adjusted in particular by adding an alkali metal hydroxide or alkaline earth metal hydroxide, such as a sodium, potassium or calcium hydroxide.

The distribution of materials may be optimized further by adapting the pH, it being possible for optimal mass transfer conditions to be set at above approximately pH 12.5.

It is also possible to further optimize the cleavage of optionally present acetyl-DAP by adapting the pH, it being possible for optimal cleavage conditions (cleavage kinetics) to be set at above approximately pH 13—depending on the amount of acetyl-DAP present.

Cellular components may be removed from the fermentation broth prior to alkalization, if appropriate. Methods of removing said cellular components are familiar to the skilled worker (e.g. separators, decanters, flocculation, filtration processes or combinations of a plurality of such process steps).

In another development of the process, the alkalized fermentation broth is thermally treated by heating to reflux temperature, for example either batchwise or continually, for example to. 90-110° C. at atmospheric pressure, or to a higher temperature at overpressure. Said thermal treatment is carried out under conditions which cause optionally present acetyl- DAP to be cleaved hydrolytically, preferably in an essentially quantitative manner. For this purpose the skilled worker may coordinate the important process parameters such as pressure, temperature and dwell time as required. The term "acetyl-DAP" comprises mono- and di-acetyl-DAP, with the mono-acetyl form usually being predominant, however. In another embodiment, said heating may be carried out in multiple stages, for example also with recovery of the released ammonia by intermediate expansion.

In another development of the process of the invention, DAP is extracted with an organic solvent having a miscibility gap with water, which is as polar as possible and stable at alkaline pH, such as in particular a polar, more specifically dipolar protic, organic solvent. Suitable solvents will be described in a section hereinbelow.

In a preferred embodiment, DAP extraction is and/or subsequent phase separation are carried out batchwise at elevated temperature. Further developments of extraction and work-up of the DAP-comprising extract will be described in a section hereinbelow.

The process of the invention is particularly suitable for working up fermentation broths from fermentation of a microorganism in a complex culture medium, for example one comprising yeast extract.

The invention also relates to a process for the fermentative production of DAP, wherein a lysine-producing microorganism is cultured under lysin-producing and, if appropriate, DAP-producing conditions and the DAP formed is isolated by applying a DAP isolation process as defined above.

Said fermentation may bei carried out in particular in a culture medium comprising complex media components. This may involve using a lysine-producing microorganism which additionally expresses lysine decarboxylase activity such as, for example, a heterologous lysine decarboxylase (LDC), i.e. a lysine decarboxylase derived from a different organism.

According to the invention, "complex nutrient or culture media" or "complex media" are media known per se that comprise complex compositions of substance mixtures, such as corn steep liquor, tryptone, bactone, soya hydrolysate and in particular yeast extract.

On the other hand it is also possible to contact a lysine-comprising fermentation broth with purified, optionally immobilized lysine decarboxylase, in order to decarboxylate lysine to give DAP, or to add a further, optionally immobilized LDC-expressing microorganism to the broth or to contact the latter therewith. Suitable processes in this connection are described in the prior art, to which reference is explicitly made hereby (cf. e.g. JP 2002-223771).

It is possible here in principle to conduct the entire isolation process described above or the fermentative production process described above or individual steps thereof batchwise as a batch or semibatch or fed batch or repeated (fed) batch process, or continuously.

The invention further relates to a process for preparing a DAP-comprising polymer, wherein DAP monomer is first fermentatively produced and isolated by a process as defined above and then polymerized together with at least one further comonomer. Said comonomer may be selected in particular from among polycarboxylic acids such as in particular dicarboxylic acids having from 4 to 12 carbon atoms, their esters and anhydrides; and also polyisocyanates such as in particular diisocyanates having a $C_2$-$C_{10}$-alkylene bridging group or cyclic bridging groups. Nonlimiting examples of suitable dicarboxylic acids are succinic acid, glutaric acid, adipic acid, pimelic acid, suberic acid, azelaic acid, sebacic acid, etc. Nonlimiting examples of suitable diisocyanates are methyl-ene diphenyl diisocyanate (MDI), toluene diisocyanate (TDI), hexamethylene diisocyanate (HDI) and isophorone diisocyanate. This results in the formation in particular of polymers of the polyamide, polyurea or polyurethane type, such as polyamide 5,10 or polyamide 5,6, for example.

The polymerization process involves adding at least one comonomer to the isolated DAP or employing a mixture of DAP and at least one comonomer from a DAP precipitation. A suitable DAP/comonomer mixture may be produced, for example, from a salt precipitation of DAP from a DAP extract worked up by means of distillation, as described above, Said comonomer is preferably a polycarboxylic acid, for example sebacic acid.

2. General Information on the Fermentative Production of Lysine or DAP 2.1 Microorganisms The present invention can be applied in principle on the work up of any DAP-comprising fermentation broth. There are also in principle no limitations whatsoever regarding the microorganisms employed in the fermentation. The latter may be naturally occurring microrganisms, microorganisms improved by means of mutation and selection, but in particular recombinantly produced microorganisms, such as fungi, but in particular bacteria. These microorganisms are capable either of producing DAP and/or DAP derivatives such as acetyl-DAP directly or at least of fermentatively producing lysine, in particular L-lysine. More specifically, a recombinant bacterium employed is capable of lysine biosynthesis via the diaminopimelate pathway ("DAP pathway"), the succinylase pathway or the dehydrogenase pathway.

These microorganisms can produce lysine, in particular L-lysine, from glucose, sucrose, lactose, fructose, maltose, molasses, starch, cellulose or from glycerol, fatty acids or vegetable oils or ethanol and preferably release at least part of the lysine produced into the extracellular space. They are preferably coryneform bacteria, mor specifically of the genus *Corynebacterium* or the genus *Brevibacterium*. Particular mention may be made of the species *Corynebacterium glutamicum* of the genus *Corynebacterium*, which species is known in the art for its ability to produce L-amino acids.

Examples of suitable strains of coryneform bacteria, which may be mentioned, are those of the genus *Corynebacterium*, in particular of the species *Corynebacterium glutamicum* (*C. glutamicum*), such as
*Corynebacterium glutamicum* ATCC 13032,
*Corynebacterium acetoglutamicum* ATCC 15806,
*Corynebacterium acetoacidophilum* ATCC 13870,
*Corynebacterium thermoaminogenes* FERM BP-1539,
*Corynebacterium melassecola* ATCC 17965
or
of the genus *Brevibacterium*, such as
*Brevibacterium flavum* ATCC 14067
*Brevibacterium lactofermentum* ATCC 13869 and
*Brevibacterium divaricatum* ATCC 14020;
or strains derived therefrom, such as
*Corynebacterium glutamicum* KFCC10065
*Corynebacterium glutamicum* ATCC21608.

The abbreviation KFCC means the Korean Federation of Culture Collection, the abbreviation ATCC denotes the American Type Strain Culture Collection, the abbreviation FERM BP denotes the collection of the National Institute of Bioscience and Human-Technology, Agency of Industrial Science and Technology, Japan.

2.2 Fermentation Procedure

Fermentation broths to be worked up according to the invention are derived, for example, from the culturing of recombinant coryneform bacteria which, via a deregulating intervention that promotes lysine biosynthesis and affects at least one lysine biosynthesis gene, have increased production of lysine, in particular L-lysine, or of a lysine-comprising mixture and/or which additionally overexpress an enzyme having lysine decarboxylase activity and accumulate DAP and/or acetyl-DAP. The latter are therefore capable of producing DAP directly.

Genes involved in lysine biosynthesis and an associated deregulatory intervention promoting lysine biosynthesis are summarized in table 1 below.

TABLE 1

Examples of deregulatable genes and gene products

| Enzyme (gene product) | Gene | Deregulation |
|---|---|---|
| Aspartokinase | ask | Elimination of feedback inhibition by point mutation (Eggeling et al., (eds.), Handbook of *Corynebacterium glutamicum*, pages 20.2.2 (CRC press, 2005)) and amplification) |
| Aspartate semialdehyde dehydrogenase | asd | Amplification |
| Dihydrodipicolinate synthase | dapA | Amplification |
| Dihydrodipicolinate reductase | dapB | Amplification |
| Tetrahydrodipicolinate succinylase | dapD | Amplification |
| Succinyl-aminoketopimelate transaminase | dapC | Amplification |
| Succinyl-diaminopimelate desuccinylase | dapE | Amplification |
| Diaminopimelate dehydrogenase | ddh | Amplification |
| Diaminopimelate epimerase | dapF | Amplification |
| Arginyl-tRNA synthetase | argS | Amplification |
| Diaminopimelate decarboxylase | lysA | Amplification |
| Pyruvate carboxylase | pycA | Elimination of feedback inhibition by point mutation (EP1108790) and amplification |
| Phosphoenolpyruvate carboxylase | ppc | Amplification |
| Glucose-6-phosphate dehydrogenase | zwf | Elimination of feedback inhibition by point mutation (US2003/0175911) and amplification |
| Transketolase | tkt | Amplification |
| Transaldolase | tal | Amplification |
| 6-Phosphogluconolactonase | pgl | Amplification |
| Fructose 1,6-bisphosphatase | fbp | Amplification |
| Homoserine dehydrogenase | hom | Attenuation by point mutation (EP1108790) |
| Phosphoenolpyruvate carboxykinase | pck | Knock-out or silencing by mutation etc. |
| Succinyl-CoA synthetase | sucC | Attenuation by point mutation (WO 05/58945) |
| Methylmalonyl-CoA mutase | | Attenuation by point mutation (WO 05/58945) |

A process for producing DAP using recombinant microorganisms having a deregulated lysine decarboxylase gene and at least one further deregulated gene, involved in lysine biosynthesis for example, has been disclosed in WO 2007/113127 to which reference is explicitly made hereby.

"Deregulation", as is apparent, should be understood in the broadest sense and comprises an increase or reduction or elimination of an enzyme activity in many different ways, for example by an increase or reduction of the copy number of enzyme molecules in the microorganism or a modification of another property that reduces lysine biosynthesis.

The enzyme lysine decarboxylase (E.C. 4.1.1.18.) catalyses decarboxylation of L-lysine to DAP. An example of said enzyme is the cadA gene product (Kyoto Encyclopedia of Genes and Genomes, Entry b4131) or the IdcC gene product (Kyoto Encyclopedia of Genes and Genomes, Entry JW0181). The use thereof for preparing recombinant microorganisms for the production of cadaverine is known to the skilled worker (cf. e.g. EP-A-1 482 055).

The skilled worker can achieve overexpression/deregulation by undertaking different measures, either individually or in combination. Thus it is possible to increase the copy number of the corresponding genes, or to mutate the promotor and regulatory regions or the ribosome binding site which is located upstream of the structural gene. Expression cassettes which are incorporated upstream of the structural gene act in the same manner. In addition, inducible promoters enable expression to be increased in the course of fermentative L-lysine production. Measures of extending the mRNA lifespan likewise improve expression. Furthermore, preventing the enzyme protein from being degraded likewise enhances enzyme activity. The genes or gene constructs may either be present in one or more plasmids having different copy numbers or be integrated and amplified in the chromosome. Alternatively, the genes in question may furthermore be overexpressed by altering the composition of the media and the culturing procedure.

The skilled worker will find instructions in this regard in, inter alia, Martin et al. (Biotechnology 5, 137-146 (1987)), Guerrero et al. (Gene 138, 35-41 (1994)), Tsuchiya and Morinaga (Bio/Technology 6, 428-430 (1988)), Eikmanns et al. (Gene 102, 93-98 (1991)), in the European patent 0472869, in U.S. Pat. No. 4,601,893, in Schwarzer and Pühler (Biotechnology 9, 84-87 (1991), Remscheid et al. (Applied and Environmental Microbiology 60, 126-132 (1994), LaBarre et al. (Journal of Bacteriology 175, 1001-1007 (1993)), in the patent application WO 96/15246, in Malumbres et al. (Gene 134, 15-24 (1993)), in the Japanese laid-open document JP-A-10-229891, in Jensen and Hammer (Biotechnology and Bioengineering 58, 191-195 (1998)), Makrides (Microbiological Reviews 60: 512-538 (1996), and in known textbooks of genetics and molecular biology.

Suitable producer strains are prepared by using expression constructs or vectors that comprise a nucleic acid sequence coding for a desired enzyme activity under the genetic control of regulatory nucleic acid sequences. Such constructs preferably comprise a promoter 5' upstream of the particular coding sequence and a terminator sequence 3' downstream and, if appropriate, further customary regulatory elements, in each case operatively linked to the coding sequence. "Operative linkage" means the sequential arrangement of promoter, coding sequence, terminator and, if appropriate, further customary regulatory elements in such a way that each of said regulatory elements can fulfil its function as required in expressing the coding sequence. Examples of operatively linkable sequences are activating sequences and also enhancers and the like. Further regulatory elements comprise selectable markers, amplification signals, origins of replication, and the like, Suitable regulatory sequences are described, for example, in Goeddel, Gene Expression Technology: Methods in Enzymology 185, Academic Press, San Diego, Calif. (1990).

The natural regulatory sequence may still be present, in addition to the artificial regulatory sequences, upstream of the actual structural gene. Genetic modification enables this natural regulation to be switched off, if appropriate, and expression of the genes to be increased or decreased. The gene construct may, however, also have a simpler structure, that is to say no additional regulatory signals are inserted upstream of the structural gene, and the natural promoter with its regulation is not deleted. Instead, the natural regulatory sequence is mutated in such a way that regulation no longer takes place, and gene expression is enhanced or diminished. The nucleic acid sequences may be present in one or more copies in the gene construct.

Examples of usable promoters are: the *Corynebacterium glutamicum* promoters ddh, amy, lysC, dapA, lysA, but also gram-positive promoters SPO2 as described in *Bacillus Subtilis and Its Closest Relatives*, Sonenshein, Abraham L., Hoch, James A., Losick, Richard; ASM Press, District of Columbia, Wash. and Patek M. Eikmanns B J. Patek J. Sahm H. Microbiology. 142 1297-309, 1996, or else cos, tac, trp, tet, trp-tet, lpp, lac, 1 pp-lac, lacIq, T7, T5, T3, gal, trc, ara, SP6, λ-PR or λ-PL promoter, which are advantageously used in gram-negative bacteria. Preference is also given to using inducible promoters such as, for example, light- and, in particular, temperature-inducible promoters such as the $P_rP_l$ promoter. It is possible in principle for all natural promoters with their regulatory sequences to be used. In addition, it is also possible advantageously to use synthetic promoters such as multiple promoters (cf. e.g. WO2006/069711).

Said regulatory sequences are intended to make specific expression of the nucleic acid sequences possible. This may mean, for example, depending on the host organism, that the gene is expressed or overexpressed only after induction or that it is immediately expressed and/or overexpressed.

The regulatory sequences or factors may moreover preferably influence positively, and thus increase or reduce, expression. Thus, enhancement of the regulatory elements can take place advantageously at the level of transcription by using strong transcription signals such as promoters and/or enhancers. However, it is also possible to enhance translation by, for example, improving mRNA stability.

An expression cassette is prepared by fusing a suitable promoter, a suitable Shine-Dalgarno sequence to a lysine biosynthesis nucleotide sequence and a suitable terminator signal. Conventional techniques of recombination and cloning are used for this purpose, as described, for example, in Current Protocols in Molecular Biology, 1993, John Wiley & Sons, Incorporated, New York N.Y., PCR Methods, Gelfand, David H., Innis, Michael A., Sninsky, John J. 1999, Academic Press, Incorporated, California, San Diego, PCR Cloning Protocols, Methods in Molecular Biology Ser., Vol. 192, 2nd ed., Humana Press, New Jersey, Totowa. T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which enables the genes to be optimally expressed in the host. Vectors are well known to the skilled worker and can be found, for example, in "Cloning Vectors" (Pouwels P. H. et al., Eds., Elsevier, Amsterdam-New York-Oxford, 1985). Vectors mean not only plasmids but also all other vectors known to the skilled worker, such as, for example, phages, transposons, IS elements, phasmids, cosmids, and linear or circular DNA. These vectors may undergo autonomous replication in the host organism or chromosomal replication.

Suitable plasmids are those which are replicated in coryneform bacteria. Numerous known plasmid vectors such as, for example, pZ1 (Menkel et al., Applied and Environmental Microbiology (1989) 64: 549-554), pEKEx1 (Eikmanns et al., Gene 102: 93-98 (1991)) or pHS2-1 (Sonnen et al., Gene 107: 69-74 (1991)) are based on the cryptic plasmids pHM1519, pBL1 or pGA1. Other plasmid vectors, such as pCLiK5MCS for example, or those based on pCG4 (U.S. Pat. No. 4,489,160) or pNG2 (Serwold-Davis et al., FEMS Microbiology Letters 66, 119-124 (1990)) or pAG1 (U.S. Pat. No. 5,158,891), may be used in the same way.

Suitable plasmid vectors are furthermore also those which help to enable the process of gene amplification by integration into the chromosome to be applied, as described, for example, by Remscheid et al. (Applied and Environmental Microbiology 60, 126-132 (1994)) in the context of duplication and. amplification of the hom-thrB operon. This method comprises cloning of the complete gene into a plasmid vector which is capable of replicating in a host (typically *E. coli*), but not in *C. glutamicum*. Examples of suitable vectors are pSUP301 (Sirnon et al., Bio/Technology 1, 784-791 (1983)), pK18mob and pK19mob (Schäfer et al., Gene 145, 69-73 (1994)), Bernard et al., Journal of Molecular Biology, 234: 534-541 (1993)), pEM1 (Schrumpf et al. 1991, Journal of Bacteriology 173: 4510-4516) and pBGS8 (Spratt et al., 1986, Gene 41: 337-342). The plasmid vector comprising the gene to be amplified is then transferred by way of transformatiion into the desired *C. glutamicum* strain. Methods of transformation are described, for example, in Thierbach et al. (Applied Microbiology and Biotechnology 29, 356-362 (1988)), Dunican and Shivnan (Biotechnology 7, 1067-1070 (1989)) and Tauch et al. (FEMS Microbiological Letters 123, 343-347 (1994)).

The acitivity of enzymes may be affected by mutations in the corresponding genes in such a way that the rate of the enzymatic reaction is partly or completely reduced. Examples of such mutations are known to the skilled worker (Motoyama H. Yano H. Terasaki Y. Anazawa H. Applied & Environmental Microbiology. 67:3064-70, 2001, Eikmanns B J. Eggeling L. Sahm H. Antonie van Leeuwenhoek. 64:145-63, 1993-94.). This measure may be used, for example, for eliminating or slowing down reactions competing with the lysine biosynthesis of the invention (Nakayama: "Breeding of Amino Acid Producing Microorganisms", in: Overproduction of Microbial Products, Krumphanzl, Sikyta, Vanek (eds.), Academic Press, London, UK, 1982).

In addition, it may be advantageous for the production of L-lysine, aside from expression and enhancement of the lysine biosnthesis genes, to enhance one or more enzymes of an upstream biosynthetic pathway, for example the pentose phosphate metabolism, citrate cycle or amino acid export.

The microrganisms used according to the invention may be cultured for production of L-lysine either continuously or batchwise in a batch or fed batch or repeated fed batch process. A summary of known cultivation methods can be found in the textbook by Chmiel (Bioprozeβtechnik 1. EinfUhrung in die Bioverfahrenstechnik [Bioprocess technology 1. Introduction to bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Braunschweig/Wiesbaden, 1994)).

The culture medium to be used must meet the requirements of the respective strains in a suitable manner. Descriptions of culture media for various microorganisms can be found in the "Manual of Methods for General Bacteriology" of the American Society for Bacteriology (Washington D.C., USA, 1981).

These media which can be employed according to the invention include usually one or more carbon sources, nitrogen sources, inorganic salts, vitamins and/or trace elements.

Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses, or other byproducts of sugar refining. It may also be advantageous to add mixtures of various carbon sources. Other possible carbon sources are oils and fats such as, for example, soybean oil, sunflower oil, peanut oil and coconut fat, fatty acids such as, for example, palmitic acid, stearic acid or linoleic acid, alcohols such as, for example, glycerol, methanol or ethanol and organic acids such as, for example, acetic acid or lactic acid.

Nitrogen sources are usually organic or inorganic nitrogen compounds or materials which comprise these compounds. Examples of nitrogen sources include ammonia in liquid or gaseous form or ammonium salts such as ammonium sulfate, ammonium chloride, ammonium phosphate, ammonium carbonate, ammonium carbamate or ammonium nitrate, nitrates, urea, amino acids or complex nitrogen sources such as corn steep liquor, soybean meal, soybean protein, yeast extract, meat extract and others. The nitrogen sources may be used singly or as a mixture.

Inorganic salt compounds which may be present in the media include the chloride, phosphate, carbonate or sulfate salts of calcium, magnesium, sodium, cobalt, molybdenum, potassium, manganese, zinc, copper and iron, and also boric acid.

It is possible to use as sulfur source inorganic sulfur-comprising compounds such as, for example, sulfates, sulfites, dithionites, tetrathionates, thiosulfates, sulfides or else organic sulfur compounds such as mercaptans and thiols.

It is possible to use as phosphorus source phosphoric acid, potassium dihydrogen phosphate or dipotassium hydrogen phosphate or the corresponding sodium salts.

Chelating agents can be added to the medium in order to keep the metal ions in solution. Particularly suitable chelating agents comprise dihydroxyphenols such as catechol or protocatechuate, or organic acids such as citric acid.

The culture media employed according to the invention normally also comprise other growth factors such as vitamins or growth promoters, which include, for example, biotin, riboflavin, thiamine, folic acid, nicotinic acid, panthothenate and pyridoxine. Growth factors and salts are often derived from complex media components such as yeast extract, molasses, corn steep liquor and the like. Suitable precursors can moreover be added to the culture medium. The exact composition of the media compounds depends greatly on the particular experiment and is chosen individually for each specific case. Information about media optimization is obtainable from the textbook "Applied Microbiol. Physiology, A Practical Approach" (editors P. M. Rhodes, P. F. Stanbury, IRL Press (1997) pp. 53-73, ISBN 0 19 963577 3). Growth media can also be purchased from commercial suppliers, for example Standard 1 (Merck) or BHI (Brain heart infusion, DIFCO) and the like.

All media components are sterilized either by heat (e.g. 1 bar of overpressure (2 bar in total) and 121° C. for 20 min) or by sterilizing filtration. The components can be sterilized either together or, if necessary, separately. All media components can be present at the start of the cultivation or optionally be added continuously or batchwise.

The temperature of the culture is normally between 15° C. and 45° C., preferably at 25° C. to 40° C., and can be kept constant or changed during the experiment. The pH of the medium should be in the range from 5 to 8.5, preferably around 7. The pH for the fermentation can be controlled during fermentation by adding basic compounds such as sodium hydroxide, potassium hydroxide, sodium bicarbonate, ammonia or aqueous ammonia or acidic compounds such as phosphoric acid, hydrochloric acid or sulfuric acid. Foaming can be controlled by employing antifoams such as, for example, fatty acid polyglycol esters, polyalkylene glycols, silicones and others (see for example Biotechnol. Progr. 2007, 23, 767-784). The stability of plasmids can be maintained by adding to the medium suitable substances having a selective effect, for example antibiotics. Aerobic conditions are maintained by introducing oxygen or oxygen-comprising gas mixtures such as, for example, ambient air into the culture. The temperature of the culture is normally from 20° C. to 45° C. The culture is continued until formation of the desired product is at a maximum. This aim is normally achieved within 10 hours to 160 hours.

The fermentation broths obtained in this way, comprising in particular L-lysine or DAP, normally have a dry matter content of from 3 to 20% by weight.

Sugar-limited fermentation is additionally advantageous, at least at the end, but especially over at least 30% of the fermentation time. This means that the concentration of utilizable sugar in the fermentation medium is kept at, or reduced to, 0 to 3 g/l during this time.

The fermentation broth is then processed further. Depending on requirements, the biomass can be removed entirely or partly by separation methods, such as, for example, centrifugation, filtration, decantation, flocculation or a combination of these methods, from the fermentation broth or left completely in it. Preference is given to removing the biomass.

2.3 Work Up of the DAP-Comprising Fermentation Broth

The fermentation broth can then be thickened or concentrated by known methods, such as, for example, with the aid of a rotary evaporator, thin-film evaporator, falling film evaporator, by reverse osmosis or by nanofiltration. If necessary, salts which may have precipitated due to the concentration procedure may be removed, for example by filtration or centrifugation. This concentrated fermentation broth can then be worked up in the manner of the invention to obtain DAP. For the work up in accordance with the present invention, such a concentration procedure is feasible, but not absolutely necessary.

According to the invention, DAP is extracted from the fermentation broth with the aid of an organic extractant. More specifically, use is made of here of an organic solvent having a miscibility gap with water that is as polar as possible and stable at alkaline pH, such as in particular a polar, dipolar protic, organic solvent. Suitable solvents are in particular cyclic or open-chain, optionally branched alkanols having from 3 to 8 carbon atoms, in particular n- and iso-propanol, n-, sec- and iso-butanol, or cyclohexanol, and also n-pentanol, n-hexanol-n-heptanol, n-octanol, 2-octanol and the mono- or polybranched isomeric forms thereof. Particular mention is to be made here of n-butanol.

In a preferred embodiment, the extraction and/or subsequent phase separation are carried out batchwise at an elevated temperature which is limited by the boiling points of water and of the extractant or of possibly forming azeotropes. Using the extractant n-butanol, extraction and phase separation could be carried out, for example, at about 25-90° C. or, preferably, at 40-70° C. For extraction, the two phases are stirred until the partition equilibrium has been established, for example over a period of from 10 seconds to 2 hours, preferably 5 to 15 min. The phases are then left to settle until they have separated completely; this takes preferably from 10 seconds to 5 hours, for example 15 to 120 or 30 to 90 minutes, in particular also at a temperature in the range from about 25-90° C. or 40-70° C. in the case of n-butanol.

In further preferred embodiments, DAP is extracted from the fermentation broth continuously in a multi-stage process (for example in mixer-settler combinations) or continuously in an extraction column.

The skilled working may establish the configuration of the extraction columns which can be employed according to the invention for the phases to be separated in each case as part of optimization routines. Suitable extraction columns are in principle those without power input or those with power input, for example pulsed columns or columns with rotating internals. The skilled worker may also, as part of routine work, select in a suitable manner types and materials of internals, such as sieve trays, and column trays, to optimize phase separation. The basic theories of liquid-liquid extraction of small molecules are well known (cf. e.g. H.-J. Rehm and G. Reed, Eds., (1993), Biotechology, Volume 3 Bioprocessing, Chapter 21, VCH, Weinheim). The configuration of industrially applicable extraction columns is described, for example, in Lo et al., Eds., (1983) Handbook of Solvent Extraction, JohnWiley& Sons, New York. Explicit reference is made to the disclosure of the textbooks above.

After phase separation, DAP is isolated and purified from the DAP-comprising extract phase in a manner known per se. Possible measures of recovering DAP are in particular, without being limited thereto, distillation, precipitation as salt with suitable organic or inorganic acids, or combinations of such suitable measures.

Distillation may be carried out continuously or batchwise. A single distillation column or a plurality of distillation columns coupled to one another may be used. Configuring the distillation column apparatus and establishing the operational parameters are the responsibilities of the skilled worker. The distillation columns used in each case may be designed in a manner known per se (see e.g. Sattler, Thermische Trennverfahren [Thermal separation methods], 2nd Edition 1995, Weinheim, p. 135ff; Perry's Chemical Engineers Handbook, 7th Edition 1997, New York, Section 13). Thus, the distillation columns used may comprise separation-effective internals, such as separation trays, e.g. perforated trays, bubble-cap trays or valve trays, arranged packings, e.g. sheet-metal or fabric packings, or random beds of packings. The number of plates required in the column(s) used and the reflux ratio are essentially governed by the purity requirements and the relative boiling position of the liquids to be separated, with the skilled worker being able to ascertain the specific design and operating data by known methods.

Precipitation as salt may be achieved by adding suitable organic or inorganic acids, for example sulfuric acid, hydrochloric acid, phosphoric acid, acetic acid, formic acid, carbonic acid, oxalic acid, etc. In another preferred embodiment, an organic dicarboxylic acid is used, forming a salt which can be used, either directly or after purification, for example by recrystallization, in a subsequent polycondensation to give the polyamide. More specifically, such dicarboxylic acids are $C_4$-$C_{12}$-dicarboxylic acids.

The organic DAP phase produced in the extraction procedure may also be worked up chromatographically. For chromatography, the DAP phase is applied to a suitable resin, for example a strongly or weakly acidic ion exchanger (such as Lewatit 1468 S, Dowex Marathon C, Amberlyst 119 Wet or others), with the desired product or the contaminants being partially or fully retained on the chromatographic resin. These chromatographic steps may be repeated, if necessary, using the same or other chromatographic resins. The skilled worker is familiar with selecting the appropriate chromatographic resins and their most effective application. The purified product may be concentrated by filtration or ultrafiltration and stored at an appropriate temperature.

The identity and purity of the compound(s) isolated may be determined by prior art technologies. These comprise high performance liquid chromatography (HPLC), gas chromatography (GC), spectroscopic methods, staining methods, thin layer chromatography, NIRS, enzyme assay or microbiological assays. These analytical methods are summarized in: Patek et al. (1994) Appl. Environ. Microbiol. 60:133-140; Malakhova et al. (1996) Biotekhnologiya 11 27-32; and Schmidt et al. (1998) Bioprocess Engineer. 19:67-70. Ullmann's Encyclopedia of Industrial Chemistry (1996) Vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Vol. 17.

The invention will now be described in more detail on the basis of the following nonlimiting examples and with reference to the accompanying figures.

EXPERIMENTAL PART

Fermentation Example 1

An aliquot of cells was taken from a stock culture of a DAP-producing strain known per se (cf. WO 2007/113127, example 2, page 14; to which reference is explicitly made hereby) (storage at −80° C.), streaked out on solid medium (particular media compositions, cf. table 2) in a Petri dish (culture 1) and then incubated at 30° C. for 72 h. The cells obtained in this way were taken up in 0.9% strength NaCl solution, streaked out again on solid medium in a Petri dish (culture 2) and then incubated at 30° C. for another 24 h. The cells were then taken from the Petri dish (culture 2) using an inoculation loop to inoculate 200 ml in a 2 l shaker flask with 2 baffles (composition similar to plate and batch media) and incubated on an orbital shaker at 250 rpm and 30° C. for 24 h.

The contents of the shaker flasks served as preculture for inoculating a 75 l fermenter with a filling volume of 50 l. The pH was regulated to pH 6.8 with the aid of gaseous ammonia. The gassing rate was approx. 0.33 vvm.

The main culture was carried out in a 5 m³ tank with a filling volume of 700 l in the batch phase. To this end, the culture was transferred from the 75 l fermenter to the 5-m³ tank after a further 24 h. The pH was regulated to pH 6.8 with ammonia. The dissolved oxygen was regulated in the range from 20 to 30% (saturation of air) by adapting the gassing rate and stirrer revolutions.

After approx. 24 h the glucose concentration of the batch medium had decreased to below 1 g/l and metering in the feed began. The final fermentation volume of approx. 3200 l was attained after approx. 80 h. The final concentrations in the fermentation were as follows: $OD_{610}$: 140, 1,5-diaminopentane: 72 g/l, lysinexHCl: 15 g/l, acetyl-diaminopentane: 10 g/l.

The cells were removed using a solid wall centrifuge, and they were concentrated by a factor of 3.3 in the turbid liquor, with turbidity in the clear liquor at approx. $OD_{610}$ 5. The clear liquor was adjusted to pH 13.5 with 50% strength NaOH.

TABLE 2

Compositions of the media

| | Plate | Flask | Preculture Batch | Main culture Batch | Main culture Feed |
|---|---|---|---|---|---|
| Agar | 20.00 g/l | | | | |
| Glucose monohydrate | 62.48 g/l | 62.48 g/l | 18.76 g/l | 62.50 g/l | 431.79 g/l |
| Ammonium sulfate | 24.29 g/l | 24.29 g/l | | 24.29 g/l | 130.00 g/l |
| Yeast extract. spray-dried | 15.16 g/l | 15.16 g/l | 18.94 g/l | 19.00 g/l | 17.40 g/l |
| Urea | | | | | 13.79 g/l |
| Citric acid monohydrate | 2.04 g/l | 2.04 g/l | 2.04 g/l | 2.04 g/l | 1.55 g/l |
| Disodium hydrogen phosphate | 1.24 g/l | 1.24 g/l | | | |
| Magnesium sulfate heptahydrate | 1.25 g/l | 1.25 g/l | 1.25 g/l | 1.25 g/l | 1.13 g/l |
| Potassium dihydrogen phosphate | 1.24 g/l | 1.24 g/l | 2.44 g/l | 2.48 g/l | 2.24 g/l |
| Calcium sulfate dihydrate | 168.00 mg/l | 168.00 mg/l | 0.17 g/l | 0.17 g/l | 0.13 g/l |
| Iron sulfate heptahydrate | 70.48 mg/l | 70.48 mg/l | 0.07 g/l | 0.07 g/l | 0.06 g/l |
| Zinc sulfate heptahydrate | 28.00 mg/l | 28.00 mg/l | 28.00 mg/l | 28.00 mg/l | 25.21 mg/l |
| Manganese sulfate monohydrate | 14.35 mg/l | 14.35 mg/l | 14.00 mg/l | 14.00 mg/l | 12.90 mg/l |
| Boric acid | 428.70 µg/l | 428.70 µg/l | 0.38 mg/l | 0.38 mg/l | 0.38 mg/l |
| Copper sulfate pentahydrate | 417.27 µg/l | 417.27 µg/l | 0.36 mg/l | 0.36 mg/l | 0.37 mg/l |
| Cobalt sulfate heptahydrate | 337.24 µg/l | 337.24 µg/l | 0.30 mg/l | 0.30 mg/l | 0.30 mg/l |
| Nickel sulfate hexahydrate | 284.37 µg/l | 284.37 µg/l | 0.24 mg/l | 0.24 mg/l | 0.25 mg/l |
| Disodium molybdate dihydrate | 71.45 µg/l | 71.45 µg/l | 0.08 mg/l | 0.08 mg/l | 0.06 mg/l |
| Pantothenic acid | 28.00 mg/l | 28.00 mg/l | 28.00 mg/l | 28.00 mg/l | 25.20 mg/l |
| Nicotinamide | 8.40 mg/l | 8.40 mg/l | 8.40 mg/l | 8.40 mg/l | 7.56 mg/l |
| Thiamine hydrochloride | 7.00 mg/l | 7.00 mg/l | 7.00 mg/l | 7.00 mg/l | 6.30 mg/l |
| Biotin | 4.20 mg/l | 4.20 mg/l | 4.20 mg/l | 4.20 mg/l | 3.78 mg/l |

All media components were sterilized at 121° C. for 30 min, except vitamins which were sterilized by filtration using a 0.2 µm filter.

Exemplary embodiment 1

Recovering DAP From Fermentation Broth of a Lysine- and DAP-Producing Microorganism a) Thermal treatment and extraction procedures (single batch)

A 1 m³ stainless steel tank was charged with 750 kg (670 l) of cell-free fermentation broth adjusted to pH 13.5 with NaOH. The reactor contents was heated to reflux temperature (approx. 103° C.) and refluxed for 5 hours. The ammonia-comprising off gas produced in the process was collected through a gas washer (with water as washing liquid). After cooling to 60° C., 140 kg of n-Butanol were fed in, followed by stirring at 60° C. for 15 minutes, and the mixture was left to settle for 2 hours. After phase separation, the lower, aqueous phase was discharged into a 1 m³ container. The organic phase was collected in another container. The aqueous phase was extracted a further two times at 60° C. with in each case 140 kg of n-butanol, after 35 l of deionized water had been added in each case.

In total, 590 kg of organic extract phases were obtained which comprised 44.2 kg of DAP (content of approx. 7.5%).

b) Distillation procedure:

A 1 m³ stainless steel tank with mounted column (4 theoretical plates) was initially charged with 900 kg of the combined organic phases from the extraction (substep a). Another 1400 kg of extract solution were fed in at constant volume, with water/n-BuOH being distilled off. The pressure was then reduced to 200 mbar and the mixture was distilled until 360 kg of bottom product remained.

This bottom product was distilled further at 40 mbar in another stainless steel tank with a volume of 400 l and mounted column with 8 theoretical plates. After a BuOH forerun and a mixed fraction, a total 155.4 kg of DAP with an average purity of 99.6% by weight were distilled over. No more than 0.4% (GC area) of the secondary component, tetrahydropyridine, was found in any one fraction.

Test Example 1

Investigating the Rate of Mass Transfer in the Extraction

Establishment of the partition equilibrium of an organic DAP extract prepared according to the invention was investigated in the 2.5 l reactor with intense stirring at 60° C. by removing a two-phase sample via the bottom valve at various time points and immediately separating the phases after demixing. Despite a certain inaccuracy due to the required sample settling time, it can be concluded that the partition happens very quickly—after 15 seconds, the sample had 98.5% of the DAP found after 5 minutes. Additional stirring for 15 minutes can therefore be considered sufficient.

Test Example 2

Investigating the Rate of Phase Separation

The rate of phase separation was investigated in a 2.5 l double-walled jacket reactor with a 3-step beam agitator and 4 baffles.

The experimental results for mixtures (in each case 4 successive extractions) with and without thermal treatment are summarized in tables 3 and 4.

TABLE 3

Phase separation times for extracting a broth containing yeast extract without thermal treatment

| Extraction (without boiling-down) | Aqueous phase [g] | 200 ml of BuOH [g] | Stirring at 400 rpm [min] | Settling time in reactor [min] | Aqueous phase [g]/ml] | Org. phase [g]/[ml] |
|---|---|---|---|---|---|---|
| 1 | 881.0 | 165.5 | 5 | 5 | 849.4/770 | 196.2/232 |
| 2 | 842.6 | 165.5 | 5 | 20 | 831.4/750 | 173.4/210 |
| 3 | 823.4 | 165.9 | 5 | 30 (3 mm of Mulm left) | 827.5/745 | 158.8/192 |
| 4 | 820.5 | 164.8 | 5 | 10 (Temp. control off, Mulm)[1)] | 806.9/720 | 175.4/212 |

[1)]Emulsion as interphase

TABLE 4

Phase separation times for extracting a broth containing yeast extract after thermal treatment (4 h, 104° C.)

| Extraction (with boiling-down) | Aqueous phase [g] | 188 ml of BuOH [g] | Stirring at 400 rpm [min] | Settling time in reactor [min] | Aqueous phase [g]/ml] | Org. phase [g]/[ml] |
|---|---|---|---|---|---|---|
| 1 | 831.4 | 166.4 (200 ml!) | 5 | 2 | 817/740 | 170.8/204 |
| 2 | 810.1 | 155.6 | 5 | 2 | 779.3/700 | 182.4/224 |
| 3 | 772.1 | 155.6 | 5 | 2 | 770.1/690 | 156.2/193 |
| 4 | 763.1 | 155.6 | 5¾ | ~2 | 766.3/780 | 149.7/186 |

Test Example 3

Boiling-Down and Acetyl-DAP Cleavage

It was observed that the producer organism additionally acetylates part of the DAP formed on either of the two amino groups.

Figure 2:
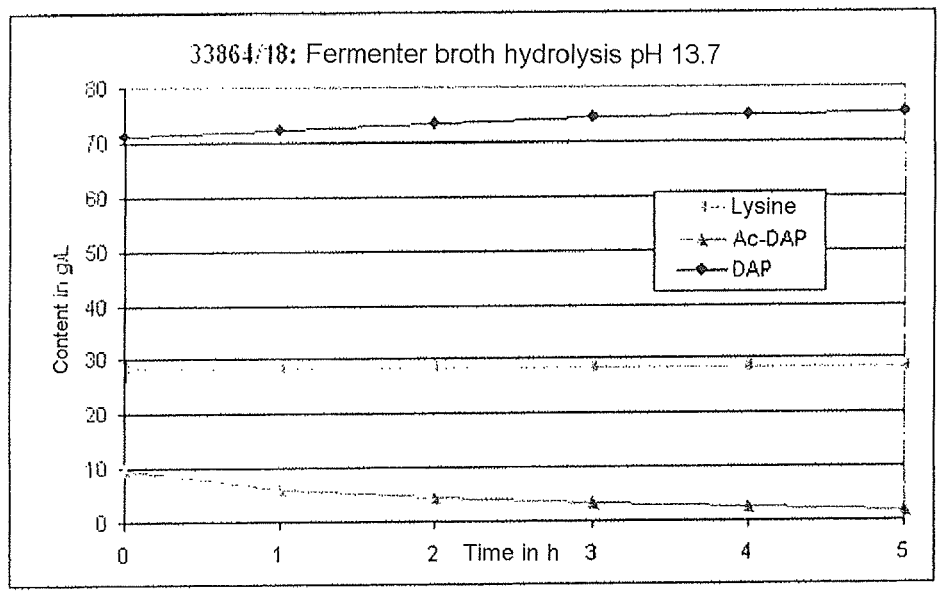
FIG. 2 illustrates the hydrolytic cleavage of acetyl-DAP (triangles) with formation of DAP (diamonds) during a five-hour thermal treatment of a fermentation broth by refluxing at pH 13.7. The residual lysine content (squares) remains unchanged during thermal treatment.

Acetyl-diaminopentane was shown to be hydrolysable by refluxing the fermentation broth, set to an alkaline pH of above 13, with liberation of diaminopentane (see FIG. 2). This enables the yield to be increased. In contrast, hydrolysis under acidic conditions (pH 1, with $H_2SO_4$) is very slow.

Figure 3:
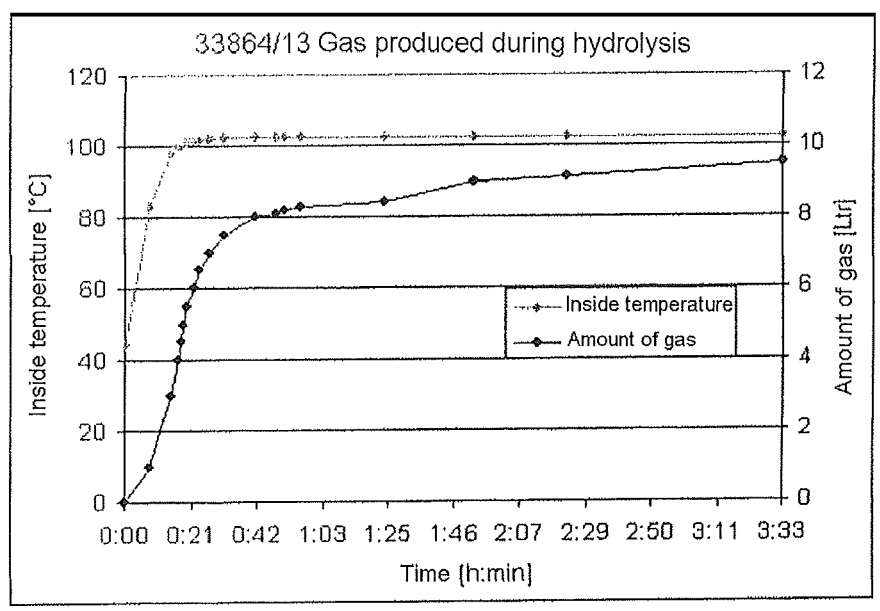
FIG. 3 illustrates the release of ammonia during the heating-up process and subsequent refluxing of the fermentation broth. Bottom curve—amount of gas; top curve—inside temperature profile.

During refluxing, reflux is seen to commence even at approx. 95° C., with a reflux temperature of approx. 103-105° C. being established in the bottoms later. The release of ammonia is observed in the hydrolysis especially during the heating-up procedure. (see FIG. 3).

A pH of at least 13.5 is particularly advantageous for successful boiling-down.

Test Example 4

Rate of Phase Separation as a Function of the Duration of Thermal Treatment

In each case 300 ml of a fermentation broth at pH 13.0, prepared according to the invention, were extracted in a 0.75 l double-walled jacket reactor with impeller stirrer, after thermal treatment, 3 times at 60° C., after stirring at 350 rpm with in each case 100 ml of n-BuOH (water-saturated). The results are summarized in table 5.

TABLE 5

Settling time after different durations of thermal treatment

| Duration of thermal treatment [h] | Settling time in reactor [min] for extraction 1/2/3 |
|---|---|
| none | 4/3(Mulm)/3(Mulm) |
| 0.5 | 3/4/5 |
| 1 | 2/3/3 |
| 2 | 2/3/3 |
| 4 | 2/2/3 |

Test Example 5 pH Dependence of the Partition Coefficient

DAP was added to in each case 2 kg of a fermentation broth prepared according to the invention to raise the DAP content to 10%, with the pH being adjusted to 11.0, 12.0 or 13.5 by adding NaOH. The partition coefficients were determined by extracting in each case five times with 150 g of water-saturated n-BuOH at 60° C. The analytically determined DAP contents of the aqueous and organic phases and the partition coefficients are listed in table 6.

TABLE 6

Partition of DAP between water and n-BuOH at various pH values

| Extraction | | 1 | 2 | 3 | 4 | 5 |
|---|---|---|---|---|---|---|
| | | | pH 13.5 | | | |
| Aqueous phase | [%] | 10.19% | 7.42% | 4.85% | 3.05% | 1.86% |
| Org. phase | [%] | 11.12% | 19.08% | 17.85% | 14.35% | 10.92% |
| K | | 1.09 | 2.57 | 3.68 | 4.71 | 5.87 |

TABLE 6-continued

Partition of DAP between water and n-BuOH at various pH values

| Extraction | | 1 | 2 | 3 | 4 | 5 |
|---|---|---|---|---|---|---|
| pH 12.0 | | | | | | |
| Aqueous phase | [%] | 7.93% | 5.44% | 3.76% | 2.67% | 1.94% |
| Org. phase | [%] | 7.40% | 14.40% | 12.90% | 10.20% | 7.40% |
| K | | 0.93 | 2.65 | 3.43 | 3.81 | 3.81 |
| pH 11.0 | | | | | | |
| Aqueous phase | [%] | 8.69% | 8.12% | 7.81% | 7.49% | 7.29% |
| Org. phase | [%] | 7.20% | 7% | 6.50% | 5.10% | 4.30% |
| K | | 0.83 | 0.86 | 0.83 | 0.68 | 0.59 |

Test Example 6 pH Dependence of the AcDAP Cleavage Kinetics

In a 0.75 l double-walled jacket reactor, in each case 500 g of fermentation broth prepared according to the invention with a hight AcDAP content were adjusted to the desired pH by adding 50% strength NaOH and heated to reflux temperature. Samples were taken after 0.5, 1, 2 and 4 h and measured by quantitative HPLC. The results are summarized in table 7.

TABLE 7 pH dependence of the rate of AcDAP cleavage

| Boiling-down [h] | pH | Lysine in each case [% by weight] | Ac-DAP | DAP | pH | Lysine in each case [% by weight] | Ac-DAP | DAP | pH | Lysine in each case [% by weight] | Ac-DAP | DAP |
|---|---|---|---|---|---|---|---|---|---|---|---|---|
| 0 | 12.99 | 0 | 2.131 | 4.405 | 13.58 | 0 | 2.027 | 4.426 | 13.98 | 0 | 1.903 | 4.051 |
| 0.5 | 13.02 | 0 | 2.011 | 4.568 | 13.52 | 0 | 1.56 | 4.877 | 13.90 | 0 | 0.439 | 5.013 |
| 1 | 12.92 | 0 | 1.908 | 4.652 | 13.48 | 0 | 1.269 | 5.089 | 13.90 | 0 | 0.145 | 5.21 |
| 2 | 12.81 | 0 | 1.791 | 4.73 | 13.42 | 0 | 0.9 | 5.363 | 13.88 | 0 | 0 | 5.327 |
| 4 | 12.61 | 0 | 1.542 | 4.827 | 13.34 | 0 | 0.508 | 5.622 | 13.88 | 0 | 0 | 5.434 |

Test Example 7

Salt Precipitation

A solution of 7.2 g of adipic acid in 70 g of water-saturated butanol was added dropwise to 130 g of an extract phase prepared according to the invention and having a DAP content of appr. 4.1% by weight at 25-30° C. The reaction mixture was cooled to 3° C., the solid was filtered off and dried in a nitrogen stream overnight. This produced 12.7 g of a white solid which was characterized by means of $^{13}$C-NMR as a 1:1 mixture of adipic acid and DAP.

Reference is made to the disclosure of the entire prior art cited herein.

The invention claimed is:

1. A process for isolating 1,5-diaminopentane (DAP) from a DAP-comprising fermentation broth, comprising
   a) alkalizing said fermentation broth by adjusting to pH>11;
   b) thermally treating said alkalized fermentation broth under conditions which cause optionally present acetyl-DAP to be cleaved hydrolytically;
   c) extracting DAP with an organic extractant; and
   d) isolating DAP,
   wherein said thermal treatment of step b) is effected for a period of time sufficient to assist phase separation in said extraction step c).

2. The process of claim 1, wherein the pH is adjusted by adding an alkali metal hydroxide or an alkaline earth metal hydroxide.

3. The process of claim 1, wherein the alkalized fermentation broth is thermally treated by heating to reflux temperature.

4. The process of claim 1, wherein DAP is extracted with a dipolar protic organic solvent.

5. The process of claim 4, wherein the extractant is an alkanol or a cycloalkanol.

6. The process of claim 1, wherein the extraction and/or a subsequent phase separation are carried out at an elevated temperature.

7. The process of claim 1, wherein cellular components are removed from the fermentation broth prior to alkalization.

8. The process of claim 1, wherein the DAP-comprising phase of the extraction step is purified by distillation or DAP is precipitated therefrom.

9. The process of claim 1, wherein the fermentation broth is derived from fermentation of a microorganism in a culture medium comprising complex media components.

10. A process for the fermentative production of 1,5-diaminopentane (DAP), comprising
   a) culturing a lysine-producing microorganism under lysine-producing conditions and/or DAP-producing conditions, and
   b) isolating the DAP formed by applying the process of claim 1.

11. The process of claim 10, wherein the fermentation is carried out in a culture medium comprising complex media components.

12. The process of claim 10, wherein the lysine-producing microorganism comprises lysine decarboxylase activity.

13. A process for the production of 1,5-diaminopentane (DAP), comprising
   a) culturing a lysine-producing microorganism under lysine-producing conditions to produce a lysine-comprising fermentation broth;
   b) contacting the lysine-comprising fermentation broth with optionally immobilized lysine decarboxylase in order to give DAP; and
   c) isolating the DAP formed by applying the process of claim 1.

14. A process for preparing a DAP-comprising polymer, comprising
   a) providing a DAP monomer which is first fermentatively produced and isolated by the process of claim 1 and
   b) polymerizing together with at least one further comonomer.

15. The process of claim 14, wherein the comonomer is selected from among polyisocyanates and polycarboxylic acids, and salts, esters and anhydrides thereof.

16. The process of claim 14, wherein at least one comonomer is added to the isolated DAP, or wherein a mixture of DAP and at least one comonomer from a DAP precipitation is employed.

17. The process of claim 16, wherein the DAP/comonomer mixture is produced by precipitation with an organic or inorganic acid.

18. The process of claim 1, wherein the pH is adjusted to pH>12.

19. The process of claim 1, wherein the alkalized fermentation broth is thermally treated for at least 0.5 hours.

20. The process of claim 3, wherein said reflux temperature corresponds to a temperature in the range of 90 to 110° C. at atmospheric pressure.

\* \* \* \* \*